US00PP19126P2

(12) United States Plant Patent
Zary

(10) Patent No.: US PP19,126 P2
(45) Date of Patent: Aug. 19, 2008

(54) FLORIBUNDA ROSE PLANT NAMED 'JACTANIC'

(50) Latin Name: *Rosa hybrida*
Varietal Denomination: JACtanic

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/824,575

(22) Filed: Jun. 29, 2007

(51) Int. Cl.
*A01H 5/00* (2006.01)

(52) U.S. Cl. ..... Plt./144

(58) Field of Classification Search ..... Plt./144
See application file for complete search history.

(56) References Cited

U.S. PATENT DOCUMENTS

PP12,918 P2 * 9/2002 Delbard ..... Plt./144

* cited by examiner

*Primary Examiner*—Wendy C. Haas
(74) *Attorney, Agent, or Firm*—Klarquist Sparkman, LLP

(57) ABSTRACT

Floribunda rose plant having flowers presented in large clusters; large flowers, petals that are white with a yellow base and upright growth habit.

1 Drawing Sheet

Genus and species: *Rosa hybrida.*
Variety denomination: 'JACtanic'.

ORIGIN OF THE INVENTION

The present invention relates to a new and distinct variety of a floribunda rose plant named 'JACtanic' which was originated by me by crossing the variety 'HARtanna' (not patented), with the variety 'Iceberg' (not patented).

BACKGROUND OF THE INVENTION

The primary objective of this breeding was to produce a new floribunda rose variety having the large clusters, upright growth and resistance to rust and powdery mildew of the female parent combined with the continuous blooming and cold hardiness of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Flowers are presented in large clusters.
2. Distinctive raspberry fragrance.
3. Vigorous upright growth on own roots.
4. Dark green, leathery, disease resistant foliage.
5. Continuous bloom during the growing season.

Asexual reproduction of this new variety by cuttings, as performed at Wasco, Calif., shows that the foregoing characteristics and distinctions come true to form and are established and transmitted through succeeding propagations.

Comparison with Parents

'HARtanna', the female parent, differs in flower color (yellow for 'HARtanna' versus white with yellow base for 'JACtanic'). 'Iceberg' differs in growth habit (rounded for 'Iceberg' versus upright for 'JACtanic'); in clusters (small for 'Iceberg' versus large clusters for 'JACtanic'); and flower size (3.5 inches in diameter for 'Iceberg' versus 4.0 inches for 'JACtanic').

Comparison with Similar Variety

'JACtanic' is believed most similar to 'Iceberg' except for growth habit (rounded versus upright for 'JACtanic'); cluster size (small versus large clusters for 'JACtanic'); and flower size (3.5 inches in diameter versus 4.0 inches for 'JACtanic').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'HARtanna' (not patented).
*Pollen parent.*—'Iceberg' (not patented).

FLOWER

Observations made from January 2006 to June 2007 from plants commencing at two to three years of age grown in a garden environment at Somis, Calif.

Blooming habit: Continuous.

Bud:

*Size.*—About 30-35 mm long and 15-20 mm in diameter when the petals start to unfurl.

*Form.*—The bud form is long, pointed ovoid.

*Color.*—When sepals first divide, bud color is White Group 155D with Yellow Group 2D at base. When half blown, the upper sides of the petals are White Group 155D with Yellow Group 2D at base and the lower sides of the petals are White Group 155D with Yellow Group 2D at base.

*Sepals.*—Color: Upper surface: Green Group 138C. Lower surface: Green Group 143C. Length: 26-32 mm. Width: 9-11 mm. Shape: Subulate. Surface texture: Hoary. There are three lightly appendaged sepals. There are two unappendaged sepals with hairy edges.

*Receptacle.*—Color: Green Group 143C. Shape: Pear. Size: Medium, about 8-10 mm long×8-10 mm wide. Surface: Smooth.

*Peduncle.*—Length: Medium, averaging about 6-12 cm. Surface: Glandular. Color: Green Group 143C. Strength: Stiff, erect.

Bloom:

*Size.*—Medium. Average open diameter is about 7-9 cm.

*Borne.*—In pyramidal clusters of 3-7 blooms.

*Stems.*—Strength: Normal. Average length is about 35-40 cm with a diameter of 6-8 mm.

*Form.*—When first open: High centered. Permanence: Outer petal edges curl slightly.

*Petalage.*—Number of petals under normal conditions: 25-30. Color: The upper sides of the inner petals are White Group 155D. The reverse sides of the inner petals are White Group 155D. The base of the petals is Yellow Group 2D. The major color on the upper sides is White Group 155D on upper two-thirds of petal, and Yellow Group 2D at base.

*Variegations.*—None observed.

*Discoloration.*—The general tonality at the end of the first day: White Group 155D. At the end of the third day: White Group 155D. Further aging: No further change.

*Fragrance.*—Moderate. Raspberry like.

Petals:

*Texture.*—Thick.

*Surface.*—Smooth.

*Shape.*—Obovate.

*Margin.*—Entire. Apex Shape: Obtuse. Base Shape: Cuneate.

*Form.*—Edges slightly quilled.

*Arrangement.*—Imbricated.

*Petaloids.*—Number: 2-5. Color: White Group 155D with Yellow Group 2D at base.

*Persistence.*—Petals drop off cleanly before drying.

*Lastingness.*—On the plant: Fair (about 7 days). As a cut flower: Fair (about 9 days).

Reproductive parts:

*Stamens.*—Number: 60-80. Length: 5-7 mm. Anthers: Length: 1 mm. Color: Greyed-Orange Group 164C. Arrangement: Regular around styles. Filaments: Color: Yellow-Green Group 149D. Length: 4-6 mm. Pollen: Color: Greyed-Orange Group N163C.

*Pistils.*—Number: 40-60. Length: 4-5 mm. Styles: Color: Green-White Group 157B. Length: 3-4 mm. Stigmas: Color: Green-White Group 157B. Length: 1 mm.

*Hips.*—None observed.

PLANT

*Form.*—Bush, hedge.

*Growth.*—Vigorous, upright.

*Age at maturity.*—Two years.

*Mature plant.*—Height: 5 ft. Width: 3½ ft.

*Rootstock.*—Own root.

Foliage: Number of leaflets on normal mid-stem leaves: 5-7.

*Size.*—Large. About 16-20 cm long×13-15 cm wide.

*Quantity.*—Abundant.

*Color.*—New foliage: Upper side: Green Group 137A. Lower side: Green Group 137C. Old foliage: Upper side: Green Group 137A. Lower side: Green Group 137C.

Leaflets:

*Size.*—About 6-8 cm long×3-5 cm wide.

*Shape.*—Broadly oval.

*Base shape.*—Cuneate.

*Apex shape.*—Cuspidate.

*Texture.*—Leathery.

*Edge.*—Serrated.

*Serrations.*—Single, small.

*Petiole.*—Color: Upper: Greyed-Purple Group 183B. Lower: Greyed-Green 194B.

*Petiole rachis.*—Color: Greyed-Green Group 194B. Underside: Smooth.

*Auricles.*—Subulate.

*Stipules.*—Length: 3-4 cm.

*Disease resistance.*—Resistant to mildew and rust and susceptible to blackspot under normal growing conditions.

*Pest resistance.*—Not observed.

*Vein color.*—Greyed-Green Group 194B.

*Venation pattern.*—Reticulate.

Wood:

*New wood.*—Color: Green Group 143C. Bark: Smooth, with occasional glands.

*Old wood.*—Color: Green Group 141C. Bark: Smooth.

Prickles:

*Quantity.*—On main canes from base: 30-35 per 150 mm of cane. On laterals from main canes: Few.

*Form.*—Hooked slightly downward.

*Length.*—10-12 mm.

*Color when young.*—Greyed-Red Group 181C.

*Color when mature.*—Greyed-Red Group 178A.

Small prickles:

*Quantity.*—On main stalks: Few. On laterals: Few. Color: Greyed-Red Group 178A.

Winter hardiness: Hardy to Zone 5.

I claim:

1. A new and distinct variety of rose plant of the floribunda class, substantially as herein shown and described, characterized particularly by a combination of flowers presented in large clusters; large petals that are white with a yellow base and upright growth habit.

* * * * *

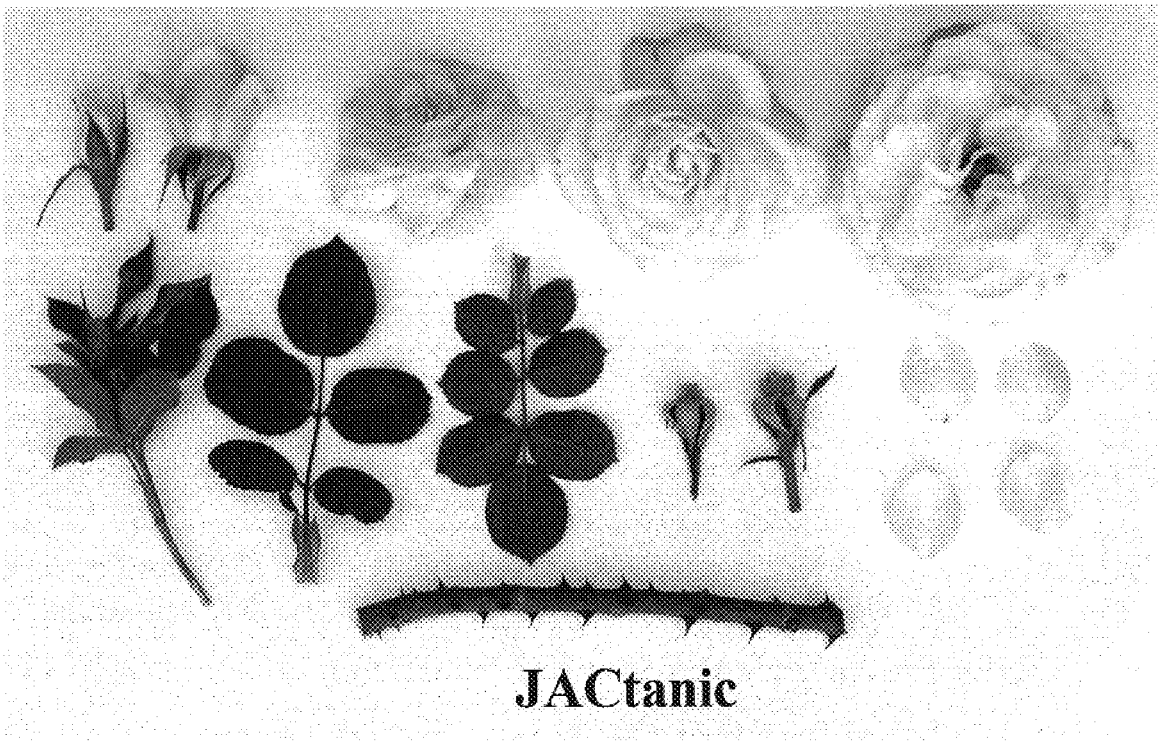
JACtanic